United States Patent
Das et al.

(10) Patent No.: US 11,559,393 B2
(45) Date of Patent: Jan. 24, 2023

(54) MULTI-PART INTRAOCULAR LENS WITH LOCKING MECHANISM

(71) Applicant: Alcon Inc., Fribourg (CH)

(72) Inventors: Kamal K. Das, Arlington, TX (US); William Jacob Spenner Dolla, Plano, TX (US)

(73) Assignee: Alcon Inc., Fribourg (CH)

( * ) Notice: Subject to any disclaimer, the term of this patent is extended or adjusted under 35 U.S.C. 154(b) by 168 days.

(21) Appl. No.: 17/189,922

(22) Filed: Mar. 2, 2021

(65) Prior Publication Data

US 2021/0275291 A1  Sep. 9, 2021

Related U.S. Application Data

(60) Provisional application No. 62/985,419, filed on Mar. 5, 2020.

(51) Int. Cl.
*A61F 2/16* (2006.01)

(52) U.S. Cl.
CPC .......... *A61F 2/1648* (2013.01); *A61F 2/1613* (2013.01); *A61F 2/1662* (2013.01); *A61F 2/16* (2013.01); *A61F 2002/169* (2015.04); *A61F 2002/1683* (2013.01); *A61F 2002/16902* (2015.04); *A61F 2250/0063* (2013.01)

(58) Field of Classification Search
CPC .... A61F 2/1613; A61F 2/1648; A61F 2/1662; A61F 2002/16902
See application file for complete search history.

(56) References Cited

U.S. PATENT DOCUMENTS

| | | | | | |
|---|---|---|---|---|---|
| 5,968,094 | A | * | 10/1999 | Werblin | A61F 2/1602 623/6.34 |
| 6,063,118 | A | * | 5/2000 | Nagamoto | A61F 2/15 623/6.12 |
| 2002/0128710 | A1 | * | 9/2002 | Eggleston | A61F 2/1613 623/6.22 |
| 2004/0148022 | A1 | * | 7/2004 | Eggleston | A61F 2/1613 623/6.22 |
| 2016/0199176 | A1 | | 7/2016 | Wanders | |
| 2017/0319332 | A1 | | 11/2017 | Kahook | |

FOREIGN PATENT DOCUMENTS

| | | |
|---|---|---|
| DE | 102017221476 A1 | 5/2019 |
| WO | 2015134058 A1 | 9/2015 |

\* cited by examiner

*Primary Examiner* — William H Matthews (57) ABSTRACT

A multi-part intraocular lens (IOL) with an interchangeable optic seated on a base and secured by a locking mechanism. The optic comprises an anterior surface with a diameter greater than a diameter of a ring of the base. The posterior side of the optic has a posterior surface, a transition region for contact with the base, and sidewalls and tabs radially outward of the transition region. The sidewalls and tabs overlap at least a portion of the ring to reduce or even prevent decentration and tilt of the optic. Each tab has a lateral extension for coupling to the base.

20 Claims, 6 Drawing Sheets

MULTI-PART INTRAOCULAR LENS WITH LOCKING MECHANISM

PRIORITY CLAIM

This application claims the benefit of priority of U.S. Provisional Patent Application Ser. No. 62/985,419 titled "MULTI-PART INTRAOCULAR LENS WITH LOCKING MECHANISM," filed on Mar. 5, 2020, whose inventors are Kamal K. Das and William Jacob Spenner Dolla, which is hereby incorporated by reference in its entirety as though fully and completely set forth herein.

TECHNICAL FIELD

The present disclosure generally relates to multi-part intraocular lenses (IOLs). More specifically, the present disclosure relates to embodiments of interchangeable optics with locking mechanisms for coupling to a base.

BACKGROUND

The human eye functions to provide vision by transmitting light through a clear outer portion called the cornea and focusing the image by way of a crystalline lens onto a retina. The quality of the focused image depends on many factors including the size and shape of the eye and the transparency of the cornea and the lens.

The crystalline lens is a transparent, biconvex structure in the eye that, along with the cornea, helps to refract light to be focused on the retina. The lens, by changing its shape, functions to change the focal distance of the eye so that it can focus on objects at various distances, thus allowing a sharp real image of the object of interest to be formed on the retina. This adjustment of the lens is known as accommodation and is similar to the focusing of a photographic camera via movement of its lenses.

Ageing or other ocular diseases cause the crystalline lens to become less transparent (e.g., cloudy), vision deteriorates because of the diminished light, which can be transmitted to the retina. This deficiency in the lens of the eye is medically known as a cataract. Currently available treatment for this condition is to surgically remove the crystalline lens from the capsular bag and placement of an artificial intraocular lens (IOL) in the capsular bag. A majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The cataractous lens, once removed, is replaced by an IOL.

SUMMARY OF THE DISCLOSURE

Embodiments of IOLs described herein include multi-part IOLs in which a base and optic components are combined. A base generally has a ring and a pair of haptics for positioning and stabilizing the ring in a capsular bag. An optic is selected based on an eye condition to be treated and then coupled to the base to complete the IOL.

In one embodiment, a base includes a ring and a pair of haptics and an optic configured for seating on an anterior surface of the ring. Sidewalls on the optic overlap the base to reduce or even prevent decentration and tilt of the optic, and tabs on the optic engage the haptics to secure the optic to the base.

A ring is formed with an anterior surface and posterior surface defining a ring thickness and an inner surface and outer surface defining a ring width. In certain embodiments, the ring may have grooves.

The optic has an anterior surface formed over the diameter of the optic. The anterior surface has a radius of curvature based on the visual outcome desired of the patient's eye. The optic also has a posterior side with a posterior surface in which the posterior surface diameter is smaller than the anterior surface diameter. The posterior side also includes a transition region for contact with the anterior surface of the ring. Sidewalls on the posterior side of the optic are located radially outward of the transition region and configured to overlap at least a portion of the base when the optic is seated on the base. The height of the sidewalls determine the overlap and is selected for reducing or even preventing tilt and decentration once the IOL is implanted in the patient. Tabs with lateral extensions are also located on the posterior side of the optic. The tabs have lateral extensions that can be positioned posterior to features on the base to lock the optic to the base. In some embodiments, these features are the haptics. In other embodiments, features are part of the base such that the features are already available for engagement by the tabs. In other embodiments, the base is formed with the features. The features may be posts or other physical extensions from the base or may be recesses or openings formed in the base.

Embodiments of IOLs described herein may provide an optic that is larger and more anteriorly positioned in the capsular bag, which may be less sensitive to decentration, reduce the incidence of negative dysphotopsia post-implantation, reduce the prevalence of glint and provide other benefits. An IOL in which an optic with sidewalls with a greater sidewall height than a ring thickness may reduce cellular proliferation referred to as the posterior capsular opacification (PCO).

Various other aspects and advantages of embodiments of the present disclosure are described in the following detailed description and drawings.

BRIEF DESCRIPTION OF THE DRAWINGS

The drawings illustrate example embodiments of the present disclosure. The drawings are not necessarily to scale, may include similar elements that are numbered the same, and may include dimensions (in millimeters) and angles (in degrees) by way of example, not necessarily limitation. In the drawings.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of .+−.10% in a stated value, numeric or otherwise, unless other variations are indicated.

The following detailed description describes various embodiments of multi-part IOLs and multi-part IOL systems. Features described with reference to any one embodiment may be applied to and incorporated into other embodiments.

I. Multi-Part IOL with Interchangeable Optic and Locking Mechanism—Overview

Figure 1:
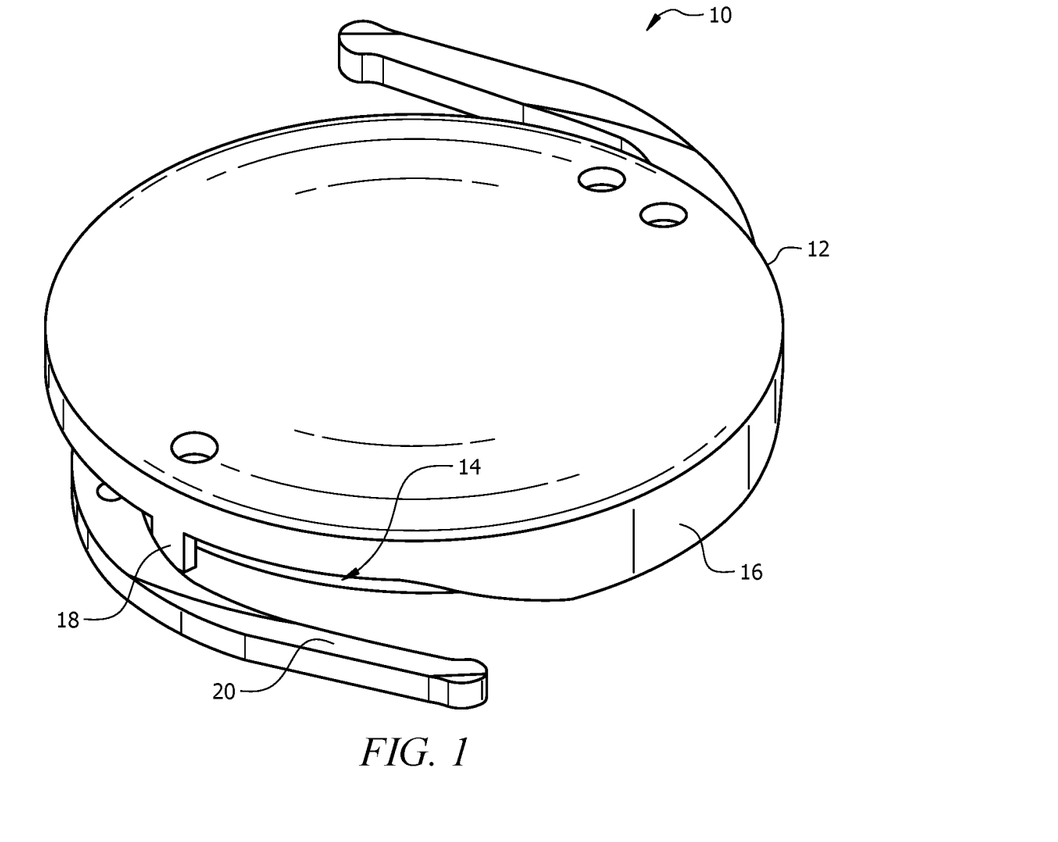
FIG. 1 is a perspective view of a multi-part IOL according to the present disclosure.

FIG. 1 depicts a multi-part intraocular lens (IOL) 10 designed for ease of insertion and assembly in a capsular bag to correct an eye condition. IOL 10 includes interchangeable optic 12 seated on top of (anterior to) base 14. FIG. 1 further depicts one sidewall 16 of a pair of sidewalls 16 on optic 12 and one tab 18 of a pair of tabs 18 positioned relative to a pair of haptics 20, which form part of a locking mechanism, discussed below in greater detail.

During surgery, a surgeon can insert and position base 14 in a capsular bag, insert optic 12 into the capsular bag, and then align and couple optic 12 to base 14 such that optic 12 is seated on base 14. Sidewalls 16 and tabs 18 formed on optic 12 overlap at least a portion of base 14 to facilitate the positioning of optic 12 on base 14 or orienting optic 12 relative to base 14 during surgery. When optic 12 is positioned on base 14, sidewalls 16 and tabs 18 reduce or even prevent tilt and decentration of optic 12.

II. Base for Supporting an Optic in a Multi-Part IOL

Figure 2:
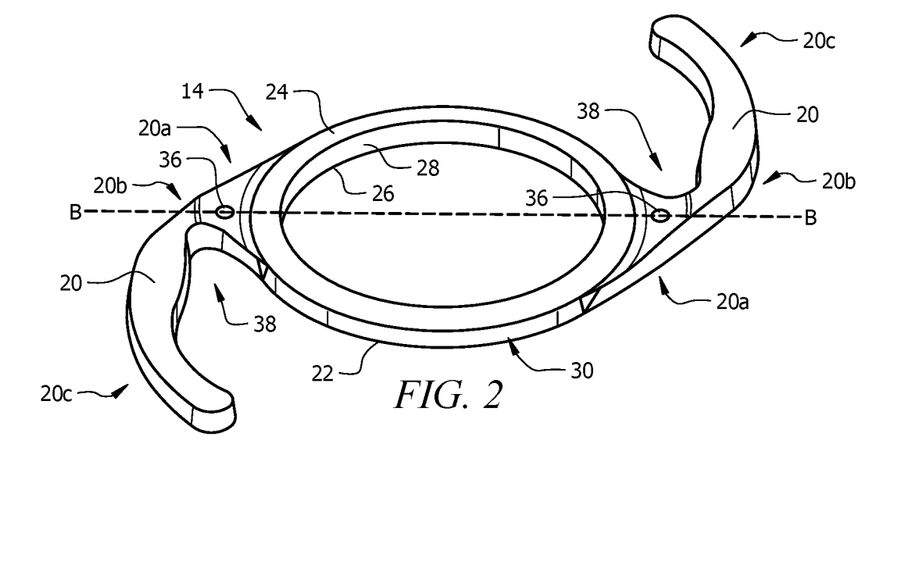
FIG. 2 is a perspective view of a base usable in the multi-part IOL shown in FIG. 1.
Figure 3:
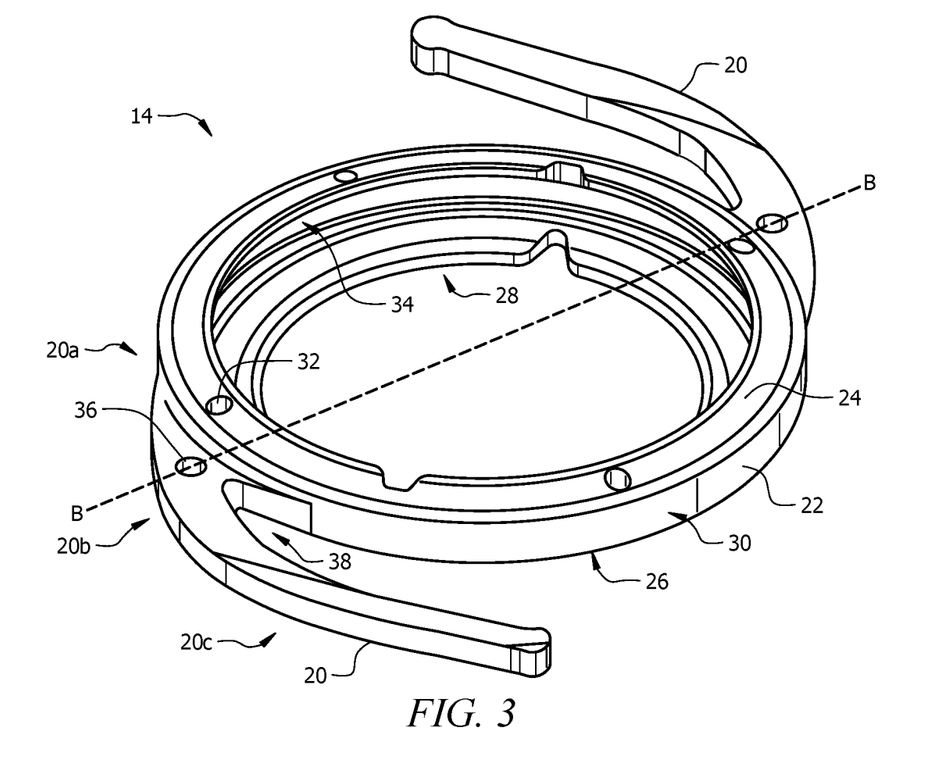
FIG. 3 is a perspective view of a base usable in the multi-part IOL shown in FIG. 1.

FIGS. 2 and 3 depict perspective views of embodiments of a base 14 for use in multi-part IOL 10. In general, various designs and configurations of base 14 include ring 22 formed with haptics 20.

As depicted in FIGS. 2 and 3, ring 22 is formed with anterior surface 24, posterior surface 26, inner surface 28 and outer surface 30. A distance between anterior surface 24 and posterior surface 26 defines a ring thickness. Outer surface 30 defines a ring circumference. Inner surface 28 and outer surface 30 define a ring width. Referring to FIG. 2, one or more of anterior surface 24, posterior surface 26, inner surface 28 and outer surface 30 may be formed as smooth, continuous surfaces. FIG. 3 depicts a type of base 14 in which one or more of anterior surface 24, posterior surface 26, inner surface 28 and outer surface 30 are formed with openings 32 that allow a surgeon to more easily insert and manipulate base 14 or assemble IOL 10. Inner surface 28 may be formed with a radially inward facing recess or groove 34 commonly used to retain other types of optics.

Referring still to FIGS. 2 and 3, base 14 includes haptics 20 coupled to ring 22. Haptics 20 are shaped for positioning and stabilizing base 14 in the capsular bag. Each of haptics 20 has a gusset region 20a, an elbow region 20b and a distal region 20c. Gusset region 20a may be configured to move an attachment location of haptics 20 radially outward from ring 22 and may have openings 36 to allow a surgeon to insert and manipulate base 14. A pair of openings 36 in haptics 20 may define an axis (B-B) for base 14, discussed in greater detail below. Distal region 20c may be configured to provide a contact area between haptics 20 and the capsular bag. Elbow region 20b may be configured to provide a flexibility of haptic 20 to allow distal region 20c to engage a capsular bag for positioning and stabilizing ring 22 in the capsular bag. An inner surface of gusset region 20a and outer surface 30 of ring 22 form ring-haptic junction 38. In some embodiments, haptics 20 and ring-haptic junctions 38 are configured to form part of a locking mechanism of IOL 10, discussed below in greater detail.

III. Optic for Seating on a Ring of the Base

Typically, if an optic (not shown) is positioned inside a ring (such as ring 22 depicted in FIG. 3), the optic will have a diameter smaller than an inner diameter of the ring. As a result, this type of optic will be more difficult to position in a ring, the optic zone will be smaller and the ring has the potential to increase glare or other effects.

Figure 4A:
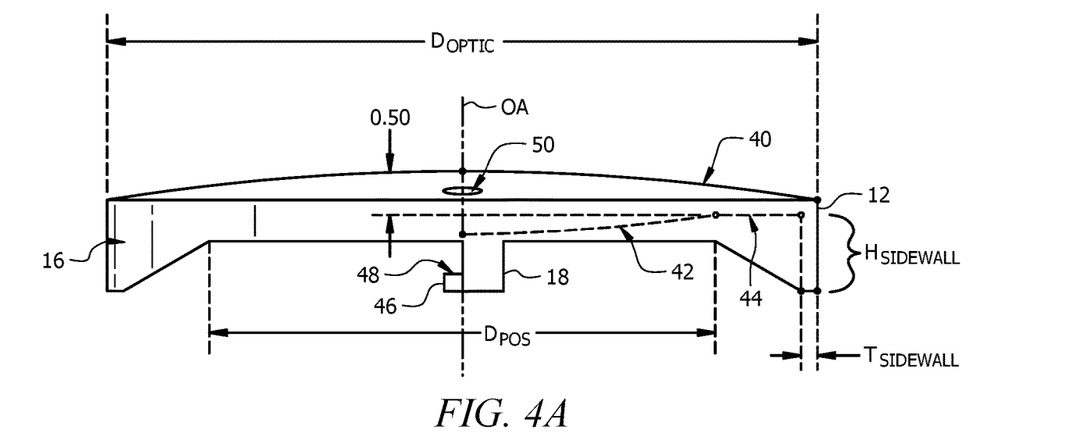
FIGS. 4A and 4B are front and side views, respectively, of an optic of the multi-part IOL shown in FIG. 1.
Figure 4B:
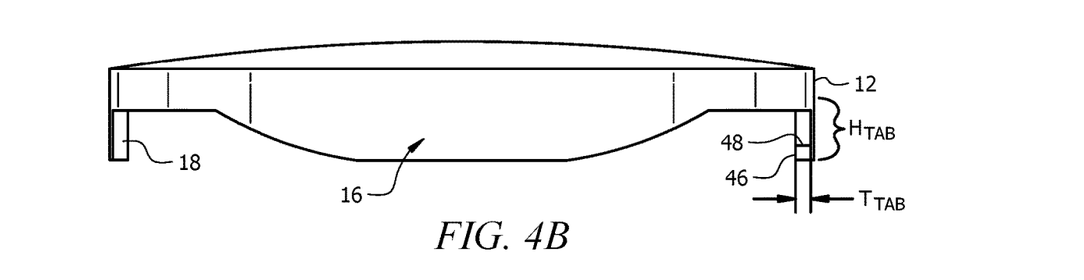

FIGS. 4A and 4B depict front and side views, respectively, of optic 12 configured with a large optic zone capable of being seated on (instead of seated in) ring 22. Referring to FIG. 4A, optic 12 comprises anterior surface 40 in which the optic portion may be defined over the optic diameter ($D_{OPTIC}$) of optic 12. Due to the optic 12 being positioned on or over the ring 22, the optic may therefore be more anteriorly positioned, as well as have a larger anterior surface 40. These features of the optic 12 may offer benefits, such as, for example, mitigating undesirable photic phenomena and reducing the prevalence of glint. In some embodiments, anterior surface includes openings 50, discussed below. Optic 12 has a posterior side with a posterior surface 42 defining a radius of curvature for a posterior optic surface diameter ($D_{POS}$) less than $D_{OPTIC}$. The posterior optic surface diameter ($D_{POS}$) may be equal to or greater than a diameter of inner surface 28 of ring 22. The posterior side of optic 12 further includes transition region 44 between posterior surface 42 and sidewalls 16. In certain embodiments, an intersection of posterior surface 42 and transition region 44 forms an angle. In certain embodiments, $D_{POS}$ of posterior surface 42 is approximately the same as a diameter of inner surface 28 of ring 22, such that the width of transition region 44 equals the width of ring 22.

Optic 12 further comprises components used for an embodiment of a locking mechanism. As depicted in FIGS. 4A and 4B, the posterior side of optic 12 includes sidewalls 16 and tabs 18 formed near the outer circumference of optic 12. Each sidewall 16 is configured with a height ($H_{SIDEWALL}$) and each tab 18 is configured with a height ($H_{TAB}$) such that sidewalls 16 and tabs 18 extend in the posterior direction to overlap a base (such as base 14 depicted in FIG. 2 or FIG. 3). Sidewalls 16 and tabs 18 may be formed with heights ($H_{SIDEWALL}$) and ($H_{TAB}$), respectively, to facilitate positioning of optic 12 on base 14 during surgery and reduce or even prevent decentration and tilt post-surgery. As depicted in FIG. 4B, the height ($H_{SIDEWALL}$) of sidewalls 16 may vary circumferentially, and each sidewall 16 may be tapered or curved to improve usability. In some embodiments, sidewalls 16 are formed with height ($H_{SIDEWALL}$) less than the thickness of ring 22 such that sidewalls 16 overlap a portion of, but do not completely cover, ring 22. In other embodiments, sidewalls 16 are formed with height ($H_{SIDEWALL}$) equal to or greater than the thickness of ring 22 such that sidewalls 16 overlap to extend a distance posterior to ring 22.

IV. Locking Mechanism for a Multi-Part IOL

IOL 10 includes a locking mechanism to facilitate optic 12 remaining seated on base 14 in a desired orientation. FIGS. 2, 3, 4A and 4B depict portions of one embodiment of a locking mechanism. Referring to FIGS. 2 and 3, ring 22 comprises haptics 20 and FIGS. 4A and 4B depict tabs 18, wherein each tab 18 includes lateral extension 46. When optic 12 is seated on ring 22, positioning lateral extensions 46 posterior to haptics 20 may lock optic 12 to base 14. In some embodiments, when optic 12 is seated on anterior surface 24 of ring 22, the height $H_{TAB}$ of tabs 18 ensures lateral extensions 46 are generally positioned posterior to haptics 20. When lateral extensions 46 are generally positioned posterior to haptics 20, rotation of optic 12 in a first direction (e.g., clockwise) relative to an optical axis (OA) positions lateral extensions 46 posterior and proximate to haptics 20 such that optic 12 and ring 22 are connected. In some embodiments, optic 12 is rotatable in the first direction until anterior surfaces 48 of lateral extensions 46 contact posterior surfaces of haptics 20 to lock optic 12 to base 14.

The locking mechanism allows optic 12 to be unlocked from base 14. To unlock optic 12 from base 14, if optic 12 and ring 22 are connected and optic 12 is rotated in an opposite direction (e.g., counterclockwise relative to optical axis OA), lateral extensions 46 may be moved from a position proximate to haptics 20 to a position that is not proximate to haptics 20 such that optic 12 and ring 22 are disconnected and optic 12 can be separated from ring 22.

V. Assembly of a Multi-Part IOL with an Interchangeable Optic and a Locking Mechanism A multi-part IOL 10, including base 14 and optic 12, may be implanted using various surgical techniques. A multi-part IOL 10 may be implanted by initially delivering base 14 into the capsular bag in a rolled configuration using an injector (a.k.a., inserter or delivery tube) inserted through a corneal incision, through the capsulorhexis, and into the capsular bag.

Base 14 may be ejected from the injector and allowed to unfurl. With gentle manipulation, haptics 20 of base 14 engage the inside equator of the lens capsule and center ring 22 relative to the capsulorhexis. Openings 36 in haptics 20 may facilitate handling of base 14 and indicate an orientation of base 14, including an axis (B-B) associated with an orientation of base 14.

Figure 5A:
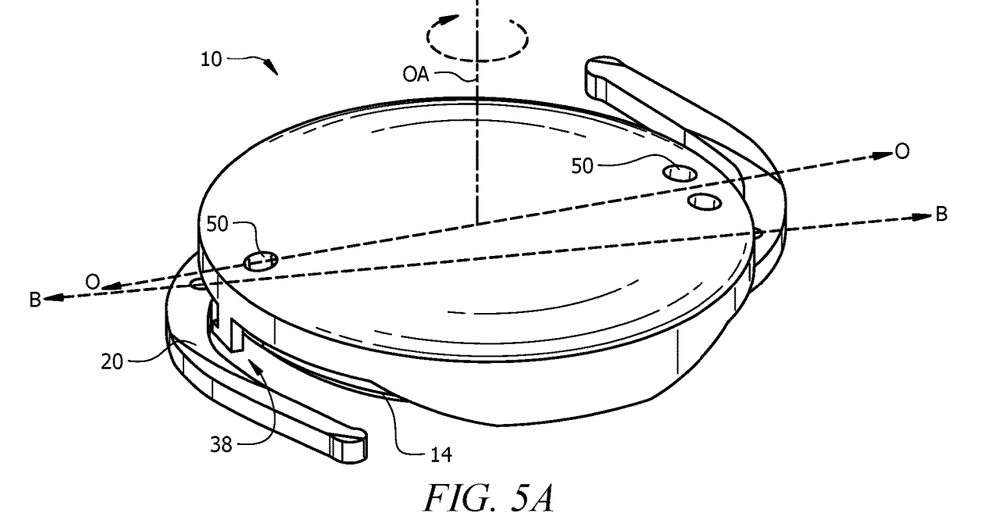
FIGS. 5A and 5B are perspective and close-up perspective views, respectively, of the multi-part IOL shown in FIG. 1.

Optic 12 may also be delivered in a rolled configuration using an injector, positioning the distal tip thereof adjacent to base 14. Optic 12 may be ejected from the injector and allowed to unfurl. With gentle manipulation, optic 12 is centered relative to the capsulorhexis. Optic 12 may have openings 50 for ease of insertion into a capsular bag, for removal of optic 12 from a capsular bag, and to help align optic 12 relative to base 14. Referring to FIG. 5A, optic 12 may have two openings 50 on one side of optic 12 and one opening 50 on an opposite side to indicate an orientation of optic 12. Openings 50 may facilitate identifying an axis (O-O) associated with an orientation of optic 12. Openings 50 may also serve as toricity markers or indicators, for further facilitating alignment of optic 12, as well as more generally IOL 10, in some embodiments.

Once optic 12 has been delivered and unfurled in the capsular bag, optic 12 may be connected to base 14.

Figure 5B:
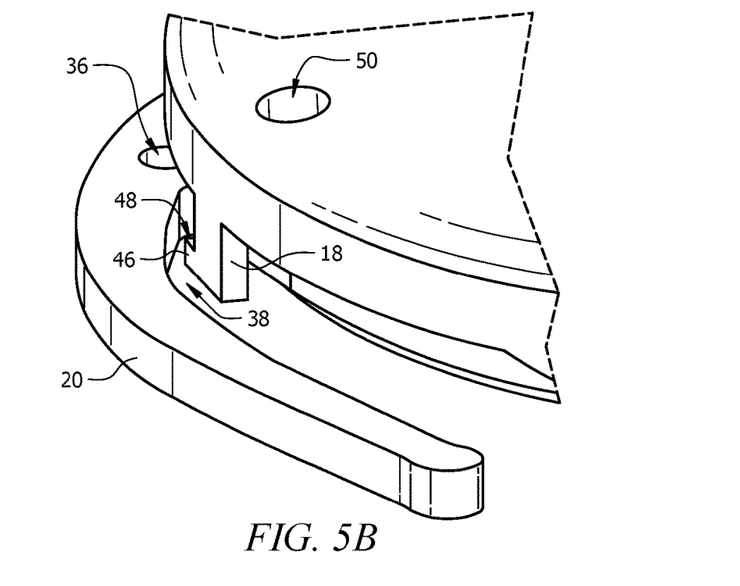

Optic 12 may be connected to base 14 by first seating optic 12 on base 14. Optic 12 may be positioned on base 14 such that sidewalls 16 overlap at least a portion of ring 22. A small force may be applied until transition region 44 contacts anterior surface 24 of ring 22. FIGS. 5A and 5B depict perspective and close-up partial perspective views, respectively, of IOL 10 with optic 12 seated on base 14.

Still referring to FIGS. 5A and 5B, once optic 12 is seated on base 14, optic 12 may be manipulated to generally position tabs 18 in ring-haptic junctions 38. With tabs 18 positioned in ring-haptic junctions 38, rotation of optic 12 relative to optical axis (OA) may position lateral extensions 46 under haptics 20. In some embodiments, positioning lateral extensions 46 under haptics 20 causes contact between anterior surfaces 48 of lateral extensions 46 and posterior surfaces of haptics 20. In the embodiment depicted in FIGS. 5A and 5B in which tabs 18 are generally positioned in ring-haptic junctions 38, a clockwise rotation of optic 12 relative to optical axis (OA) will position lateral extensions 46 posterior to haptics 20 such that anterior surfaces 48 contact posterior surfaces of haptics 20.

Referring to FIGS. 3 and 5A, base 14 may have a first axis (B-B) and optic 12 may have a second axis (O-O). Base 14 may be inserted in the capsular bag and manipulated to orient first axis (B-B). Openings 36 on base 14 may facilitate insertion and manipulation of base 14, which may include orienting first axis (B-B). Furthermore, openings 50 on optic 12 may facilitate insertion and manipulation of optic 12, including aligning second axis (O-O) relative to first axis (B-B) to align optic 12 relative to base 14.

If needed, IOL 10 including optic 12 and base 14 may be removed by generally reversing the steps described above. Removal of IOL 10 begins by rotating optic 12 relative to base 14 to disengage tabs 18 from haptics 20. In the embodiment depicted in FIGS. 5A and 5B, a counterclockwise rotation of optic 12 will disengage lateral extensions 46 from haptics 20 such that lateral extensions 46 are posterior to—but not proximate to—haptics 20.

A probe or similar device may enter the capsular bag containing multi-part IOL 10. A probe or similar device may engage openings 50 in optic 12 and rotate optic 12. As optic 12 is rotated, lateral extensions 46 disengage from haptics 20. With gentle manipulation, optic 12 may be lifted such that optic 12 and base 14 are disconnected. The probe may remove one or more of optic 12 and base 14.

VI. Alternative Locking Mechanisms

Figure 6:
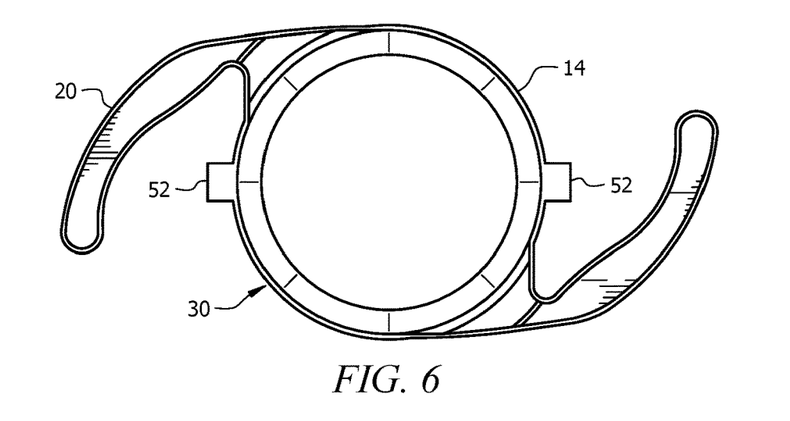
FIGS. 6-8 are top views of a base for a multi-part IOL, illustrating alternative locations for a locking mechanism.
Figure 7:
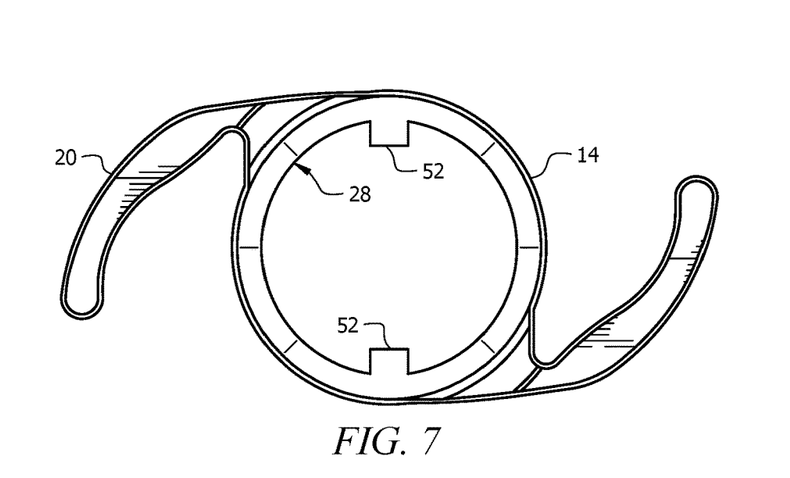
Figure 8:
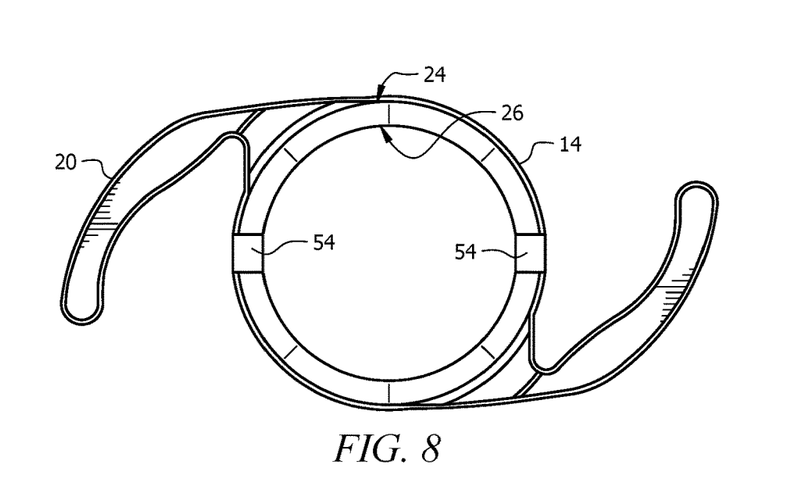

Tabs 18 with lateral extensions 46 engaging haptics 20 provide an interlocking connection between base 14 and optic 12. More generally, one or more interlocking connections may be provided between base 14 and optic 12. Each interlocking connection may include a pair of interlocking members, wherein one or both of the interlocking members are actuatable. FIGS. 6-8 depict embodiments of base 14 formed with features usable in locking mechanisms for IOL 10.

Referring to FIG. 6, a pair of posts 52 may be formed on outer surface 30 of ring 22. Optic 12 (not shown in FIG. 6) may be configured with tabs 18 as described above with respect to FIGS. 4A and 4B. Optic 12 may be seated on base 14 and rotated as described above. However, instead of lateral extensions 46 engaging haptics 20, lateral extensions 46 engage posts 52 exterior to ring 22. Referring to FIG. 7, a pair of posts 52 may be formed on inner surface 28 of ring 22. Optic 12 (not shown) may be configured with tabs 18 located radially inward of transition region 44. Optic 12 may be seated on base 14 and rotated as described above. However, instead of lateral extensions 46 engaging haptics 20, lateral extensions 46 engage posts 52 in the interior of ring 22.

Referring to FIG. 8, a pair of openings 54 may be formed in ring 22. Tabs 18 may be formed in transition region 44 of optic 12 (not shown). When optic 12 is seated on base 14, tabs 18 extend through openings 54 such that rotation of optic 12 relative to ring 22 causes lateral extensions 46 to engage posterior surface 26 of ring 22.

An advantage to the embodiments depicted in FIGS. 6-8 may be that optic 12 can be coupled to base 14 without using haptics 20, even if haptics 20 are present. Furthermore, in embodiments with tabs 18 radially inward of the optic diameter ($D_{OPTIC}$), sidewalls 16 can span a larger portion of the circumference to provide additional stability and other benefits.

Figure 9:
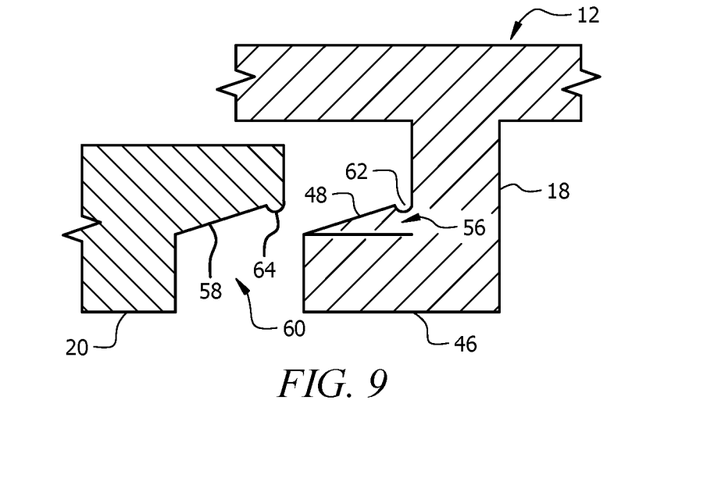
FIG. 9 is a close-up partial view of an IOL with an alternative locking mechanism.

Referring to FIG. 9, IOL 10 may utilize a locking mechanism in which anterior surfaces 48 of lateral extensions 46 are angled, as indicated by angle 56. Rotation of optic 12 relative to base 14 contacts anterior surfaces 48 of lateral extensions 46 with posterior surfaces 58 of haptics 20. Continued rotation generates a tensile force in tab 18, which may assist in seating optic 12 on base 14.

FIG. 9 also depicts notch 60 formed on the haptic 20. Notch 60 may receive tab 18 and lateral extension 46 such that tab 18 is flush with (i.e., does not extend past) the posterior surface of haptic 20 when optic 12 is seated on base 14 and lateral extensions 46 are positioned in notches 60.

FIG. 9 further depicts lateral extension 46 with recess 62, which may correspond to a raised feature 64 on a corresponding mating feature of haptic 20. Raised feature 64 positioned in recess 62 restrains or even prevents optic 12 from decoupling from base 14.

VII. Multi-Part IOLs Support Additional Optics

Figure 10:
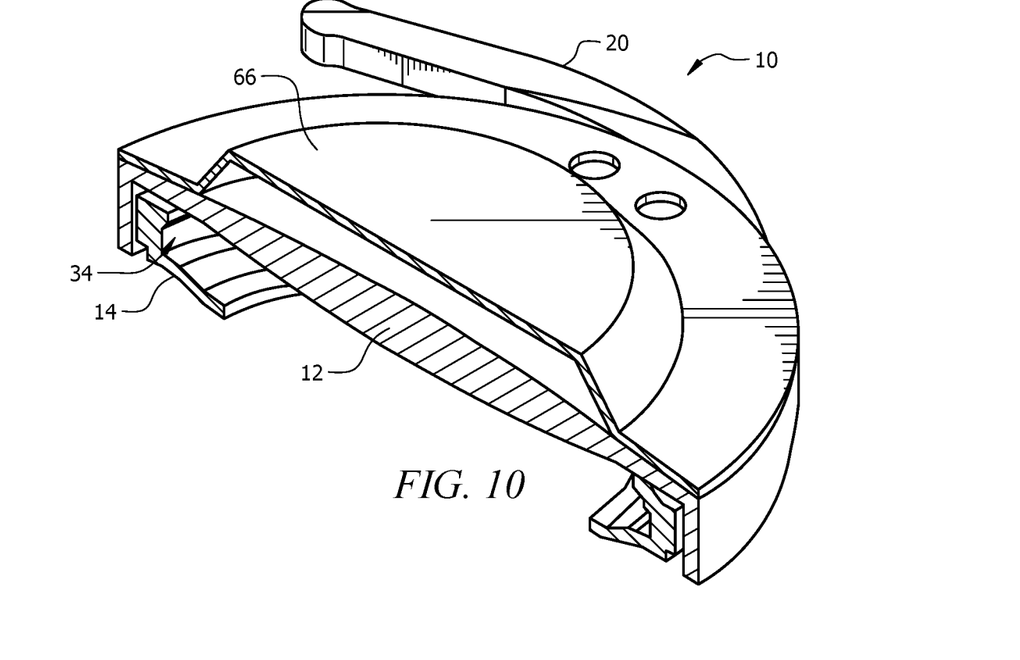
FIG. 10 is a perspective view of the multi-part IOL shown in FIG. 1 with an additional optic.

Referring to FIG. 10, embodiments described herein allow for other optic components to be added to IOL 10. As depicted in FIG. 10, IOL 10 includes optic 12 seated on base 14, and further depicts second optic 66 seated on (first) optic 12. Using techniques and features described above, a surgeon can insert base 14, insert and couple (first) optic 12 to base 14 and insert and couple second optic 66 to (first) optic 12. Furthermore, base 14 depicted in FIG. 10 comprises groove 34 such that another optical component (not shown) can be supported by base 14. The capability of having multiple optical components in a stable structure, with an increased optic zone, increases the usability of multi-part IOLs 10 for treatment of eye conditions. Furthermore, IOL 10 may be assembled such that haptics 20 are not necessary for adding second optic 66.

In general, multi-part IOL 10, comprising base 14 and optic 12, including the alternative embodiments described herein, allows for optic 12 to be adjusted or exchanged while leaving base 14 in place, either intra-operatively or post-operatively. Examples of instances where this may be desirable include, without limitation: exchanging optic 12 to correct a suboptimal refractive result detected intra-operatively; exchanging optic 12 to correct a suboptimal refractive result detected post-operatively (residual refractive error); rotationally adjusting optic 12 relative to base 14 to fine tune tonic correction; laterally adjusting optic 12 relative to base 14 for alignment of optic 12 with the true optical axis (which may not be the center of the capsular bag); and exchanging optic 12 to address the changing optical needs or desires of the patient over longer periods of time. Examples of the latter instance include, but are not limited to: an adult or pediatric IOL patient whose original optical correction needs to be changed as s/he matures; a patient who wants to upgrade from a monofocal IOL to a premium IOL (toric, multifocal, accommodating or other future lens technology); a patient who is not satisfied with their premium IOL and wants to downgrade to monofocal IOL; and a patient who develops a medical condition where an IOL or a particular type of IOL is contra-indicated.

By way of example, not necessarily limitation, an IOL according to embodiments of the present disclosure may be used to treat cataracts, large optical errors in myopic (near-sighted), hyperopic (far-sighted), and astigmatic eyes, ecto-pia lentis, aphakia, pseudophakia, and nuclear sclerosis. However, for purposes of description, the IOL embodiments of the present disclosure are described with reference to cataracts, which often occurs in the elderly population.

The foregoing discussion of the disclosure has been presented for purposes of illustration and description. The foregoing is not intended to limit the disclosure to the form or forms disclosed herein. Although the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. An intraocular lens assembly, comprising:
   a base comprising:
      a ring comprising:
         an anterior surface and a posterior surface defining a ring thickness;
         an outer surface defining a ring diameter; and
         a pair of haptics extending from the outer surface of the ring, each haptic comprising a gusset region, an elbow region and a distal region, wherein an inner surface of the gusset region and the outer surface of the ring form a ring-haptic junction; and
   an optic comprising:
      an anterior side with an anterior surface defining an anterior surface diameter greater than the ring diameter;
      a posterior side comprising:
         a posterior surface;
         a transition region radially outward of the posterior surface;
         a pair of sidewalls located radially outward of the transition region, wherein each sidewall has a sidewall height; and
         a pair of tabs located radially outward of the transition region, wherein:
            each tab defines a tab height;
            each tab comprises a lateral extension; and
            a tab positions the lateral extension posterior to a posterior surface of a haptic of the pair of haptics when the tab is positioned in the ring-haptic junction.

2. The intraocular lens assembly of claim 1, wherein the sidewall height is greater than the ring thickness.

3. The intraocular lens assembly of claim 1, wherein:
   the pair of haptics define a first axis; and
   the pair of tabs are arranged on a second axis;
   wherein positioning each tab in the ring-haptic junction aligns the second axis with the first axis.

4. The intraocular lens assembly of claim 3, wherein:
   a first pair of openings on the haptics defines the first axis;
   a second pair of openings on the optic defines the second axis; and
   aligning the second pair of openings on the optic relative to the first pair of openings on the haptics aligns the second axis with the first axis.

5. The intraocular lens assembly of claim 1, wherein:
   each lateral extension comprises an anterior surface; and rotation of the optic relative to the base when the tab is positioned in the ring-haptic junction positions the tab proximate to the haptic for contact between the anterior surface of the lateral extension and the posterior surface of the haptic.

6. The intraocular lens assembly of claim 1, wherein an inner surface of the ring comprises a groove.

7. The intraocular lens assembly of claim 6, further comprising a second optic positioned in the groove.

8. The intraocular lens assembly of claim 1, wherein:
each haptic comprises a notch for receiving the lateral extension of each tab.

9. The intraocular lens assembly of claim 1, wherein the anterior surface of each lateral extension comprises a recess for receiving a raised feature.

10. An intraocular lens (IOL) assembly, comprising:
a base comprising:
a ring comprising:
an anterior surface and a posterior surface defining a ring thickness;
an outer surface defining a ring diameter; and
a pair of posts extending radially from the ring;
an optic comprising:
an anterior side with an anterior surface defining an anterior surface diameter greater than the ring diameter;
a posterior side comprising:
a posterior surface with a posterior surface radius of curvature;
a transition region radially outward of the posterior surface;
a pair of sidewalls located radially outward of the transition region, wherein each sidewall has a sidewall height; and
a pair of tabs extending in a posterior direction, wherein:
each tab defines a tab height;
each tab comprises a lateral extension; and
the pair of tabs position the lateral extensions posterior to the pair of posts when the optic is seated on the base.

11. The IOL assembly of claim 10, wherein:
the pair of posts extend radially outward from the outer surface of the ring;
the pair of tabs are located radially outward of the posterior surface of the optic;
the pair of tabs position the lateral extensions posterior to the pair of posts when the optic is seated on the base; and
rotation of the optic relative to the base contacts an anterior surface of each lateral extension with a posterior surface of one post of the pair of posts.

12. The IOL assembly of claim 10, wherein:
the posts extend radially inward from an inner surface of the ring;
the pair of tabs are located on the posterior surface of the optic;
the pair of tabs position the lateral extensions posterior to the pair of posts when the optic is seated on the base; and
rotation of the optic relative to the base contacts an anterior surface of each lateral extension with a posterior surface of one post of the pair of posts.

13. The IOL assembly of claim 10, wherein:
the pair of posts define a first axis; and
the pair of tabs define a second axis;
wherein coupling the pair of tabs with the pair of posts aligns the second axis with the first axis.

14. The IOL assembly of claim 10, wherein:
the base further comprises a pair of haptics extending from the outer surface of the ring.

15. The IOL assembly of claim 10, wherein an inner surface of the ring comprises a groove.

16. The IOL assembly of claim 15, further comprising a second optic positioned in the groove.

17. The IOL assembly of claim 10, wherein a width of the transition region and a width of the ring are substantially equal.

18. A method for assembling an intraocular lens (IOL) comprising an optic and a base, the base comprising a ring having an anterior surface and a posterior surface defining a ring thickness, an outer surface defining a ring diameter, and a pair of haptics extending from the outer surface, the method comprising:
positioning the optic on the ring, comprising:
positioning a posterior side of the optic in contact with the anterior surface of the ring, wherein the optic comprises a pair of sidewalls radially outward of the outer surface of the ring, wherein each sidewall has a sidewall height configured to overlap at least a portion of the ring when the optic is seated on the ring;
positioning each tab of a pair of tabs on the optic relative to a ring-haptic junction in the base, wherein:
each haptic comprises a gusset region, an elbow region and a distal region,
an inner surface of the gusset region and the outer surface of the ring form the ring-haptic junction,
each tab defines a tab height;
each tab comprises a lateral extension; and
each tab positions the lateral extension posterior to a posterior surface of a haptic of the pair of haptics when the tab is positioned in the ring-haptic junction; and
rotating the optic relative to the base to position the lateral extension proximate to the posterior surface of a haptic of the pair of haptics.

19. The method of claim 18, wherein rotating the optic relative to the base to position the lateral extension proximate to the posterior surface of the haptic causes contact between an anterior surface of the lateral extension and the posterior surface of the haptic.

20. The method of claim 19, wherein one or more of the anterior surface of the lateral extension and the posterior surface of the haptic comprises an angled surface, wherein rotating the optic relative to the base to position the lateral extension proximate to the posterior surface of the haptic generates a tensile force in the tab.

* * * * *